(12) United States Patent
Maier

(10) Patent No.: US 9,320,720 B2
(45) Date of Patent: Apr. 26, 2016

(54) CONTROLLABLE THERAPEUTIC SYSTEM

(75) Inventor: Stephan Maier, Leverkusen (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 335 days.

(21) Appl. No.: 13/126,659

(22) PCT Filed: Oct. 14, 2009

(86) PCT No.: PCT/EP2009/007362
§ 371 (c)(1),
(2), (4) Date: Jun. 27, 2011

(87) PCT Pub. No.: WO2010/049062
PCT Pub. Date: May 6, 2010

(65) Prior Publication Data
US 2011/0319701 A1 Dec. 29, 2011

(30) Foreign Application Priority Data
Oct. 30, 2008 (DE) .......... 10 2008 053 889

(51) Int. Cl.
*A61K 9/70* (2006.01)
*A61K 9/00* (2006.01)

(52) U.S. Cl.
CPC .......... *A61K 9/7023* (2013.01); *A61K 9/0009* (2013.01)

(58) Field of Classification Search
CPC ......... A61N 2/02; A61N 2/008; A61N 2/004; A61K 9/0014; A61K 9/10; A61K 9/14; A61K 9/7023; A61K 9/0009; A61K 47/48861; A61K 9/5094; A61M 37/00; A61M 35/00; B82Y 30/00
USPC ................. 600/15; 604/20, 304, 307; 606/41
See application file for complete search history.

(56) References Cited

U.S. PATENT DOCUMENTS

| 4,489,711 A | 12/1984 | Latzke |
| 5,547,049 A * | 8/1996 | Weiss et al. ............... 188/267.2 |
| 2003/0146529 A1 | 8/2003 | Chen et al. |
| 2005/0118102 A1 | 6/2005 | Xiang et al. |

(Continued)

FOREIGN PATENT DOCUMENTS

| DE | 102008060708 A1 * | 6/2010 |
| EP | 1 658 861 | 5/2006 |

(Continued)

OTHER PUBLICATIONS

Dingier, A., Blum, R.P., Niehus, H., Muller, R.H., Gohla, S. "Solid lipid nanoparticles (SLNTM/LipopearlsTM)—a pharmaceutical and cosmetic carrier for the application of vitamin E in dermal products." 1999. J. Microencapsulation, vol. 16, No. 6, pp. 751-767.*

(Continued)

*Primary Examiner* — Christine H Matthews
(74) *Attorney, Agent, or Firm* — Frommer Lawrence & Haug LLP

(57) ABSTRACT

A therapeutic system, designed as a laminate and including at least one adhesive laminate layer is described. Also described is a therapeutic device having such a therapeutic system. For this purpose, at least one laminate layer or one intermediate layer and/or one intermediate layer arranged between two laminate layers contains superparamagnetic nanoparticles. The therapeutic device having such a therapeutic system includes at least one electrically controllable system which is detachably connected to the therapeutic system. The electrically controllable system has a frequency-dependent electric resistance. During operation of the therapeutic device, the electrically controllable system generates an electric or magnetic field, which can be varied in orientation and intensity over time and penetrates the superparamagnetic nanoparticles. This provides a controllable therapeutic system that is independent of contact surfaces, and a therapeutic device having such a controllable therapeutic system.

32 Claims, 4 Drawing Sheets

(56) References Cited

U.S. PATENT DOCUMENTS

Figure 1:
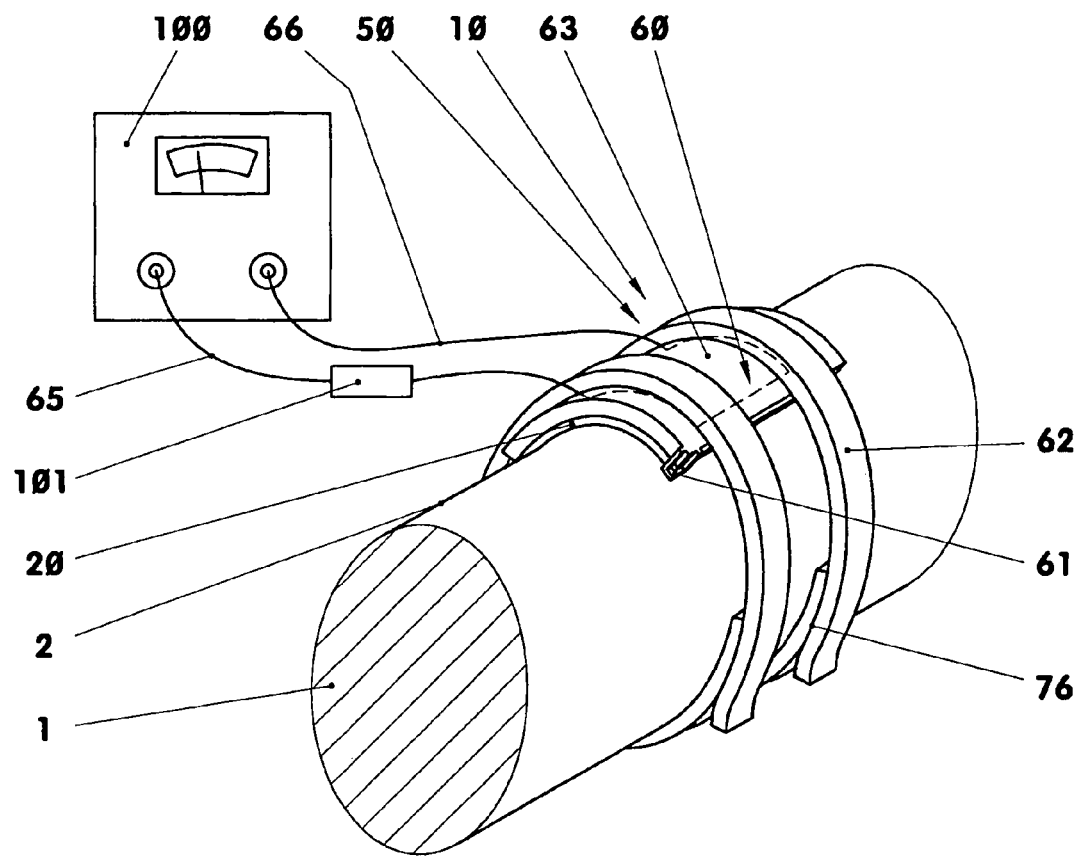

2007/0224454 A1* 9/2007 Ingvarsson et al. ............ 428/827
2009/0318846 A1* 12/2009 Prausnitz et al. ............... 604/20

FOREIGN PATENT DOCUMENTS

| | | |
|---|---|---|
| GB | 2 052 993 | 2/1981 |
| WO | WO 02/100386 | 12/2002 |
| WO | WO 2008/070459 | 6/2008 |

OTHER PUBLICATIONS

QA Pankhurst, J Connolly, SK Jones, J Dobson, "Applications of magnetic nanoparticles in biomedicine," Journal of Physics D: Applied Physics, vol. 36, pp. R167-R181 (2003).*

Pankhurst, Q.A., Connolly, J., Jones, S.K., Dobson, J., "Applications of magnetic nanoparticles in biomedicine," J. Phys. D: Appl. Phys. 36 (2003), pp. R167-R181.*

Babincova, M., Cicmanec, P., Altanerova, V., Altaner, C., Babinec, P., "AC-magnetic field controlled drug release from magnetoliposomes: design of a method for site-specific chemotherapy," Bioelectrochemistry 55 (2002) 17-19.*

Jordan, A., Scholz, R., Wust, P., Fahling, H., Felix, R., "Magnetic fluid hyperthermia (MFH):Cancer treatment with AC magnetic field induced excitation of biocompatible superparamagnetic nanoparticles," Journal of Magnetism and Magnetic Materials 201 (1999) 413-419.*

Int'l Search Report, dated Jan. 13, 2010, 2 pgs.

* cited by examiner

CONTROLLABLE THERAPEUTIC SYSTEM

The invention relates to a therapeutic system, which has a laminate design and comprises at least one adhesive laminate layer, and also to a therapy device with such a therapeutic system.

Laminated therapeutic systems include e.g. patches, which, when used, are stuck onto the skin of the patient. These patches can contain pharmaceutical active-ingredients, or can be embodied without an active ingredient. In the case of active-ingredient-containing therapeutic systems, the active ingredients penetrate into or through the skin of the patient when used. Patches in which the active ingredient penetrates the skin are referred to as transdermal therapeutic systems, for example.

When therapeutic systems are used, the temperature of the therapeutic system and/or the temperature of the receiving body affect(s) the effect of the therapy. By way of example, a temperature increase in the system leads to an increased diffusion coefficient of the active ingredients in the preparations and hence to an improved active-ingredient delivery. Furthermore, increasing the temperature of the system can improve the solubility of active ingredients in the preparation. Thus, a further part of the active ingredient may be dissolved by a temperature increase in the case of formulations that have a component that is an undissolved active ingredient. The concentration of the active ingredient in the formulation is thereby increased. This increases the thermodynamic force of the system, and thus the endeavor to deliver the active ingredient to the skin.

An increase in the temperature of the skin surface can likewise accelerate the active-ingredient absorption into the skin and through the skin. Both measures can bring about an increased effect of the drug.

WO 02/100386 A1 has disclosed a therapy device with a therapeutic system, the temperature of which can be changed. The heat transfer to the therapeutic system or to the skin is brought about by means of contact heat and/or radiant heat. In the case of heat transfer by contact, there is a need for a tight and complete contact between the heat source and the therapeutic system over the entire area. Unevenness or interruptions in the contact surface can lead to disruptions in the heat transfer.

In the case of heat transfer by heat radiation, e.g. by means of infrared radiation, the amount of heat transferred depends on the distance between the radiation source and the therapeutic system. Furthermore, the angle between the radiation source and the system surface has an influence on the quality of the heat transfer. Reflection effects and varying distances due to unevenness, folds and the curving shape of the body lead to uneven and hence poorly controllable heat supply.

Therefore, the present invention is based on the problem of developing a therapeutic system, which is independent of contact surfaces and can be controlled by temperature change, and a therapy device with such a controllable therapeutic system.

This problem is solved by the features of the main claim. To this end, at least one laminate layer or an and/or an intermediate layer, arranged between two laminate layers, of the therapeutic system contain(s) superparamagnetic nanoparticles. The therapy device with this therapeutic system comprises at least one system that can be actuated electrically in a time-varying fashion and is detachably connected to the therapeutic system. The electrically actuatable system has a frequency-dependent electrical resistance. During the operation of the therapy device, the electrically actuatable system generates an electric or magnetic field, which varies over time in orientation and magnitude and which penetrates the superparamagnetic nanoparticles.

Further details of the invention emerge from the dependent claims and the following description of schematically illustrated embodiments.

Figure 2:
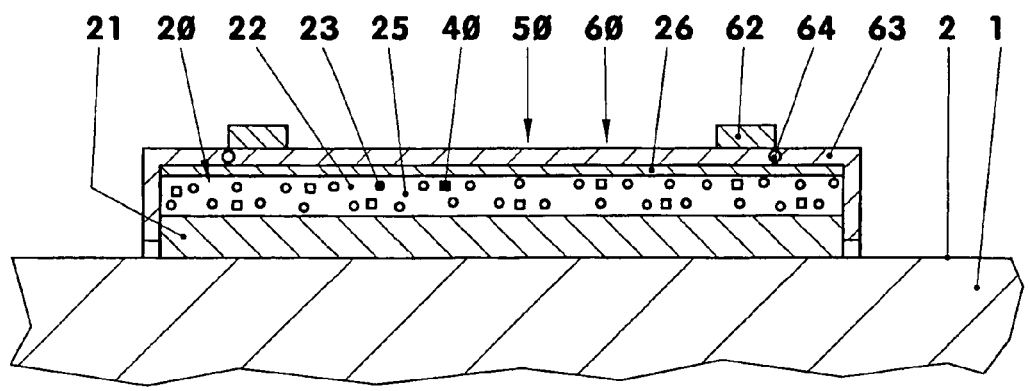
Figure 3:
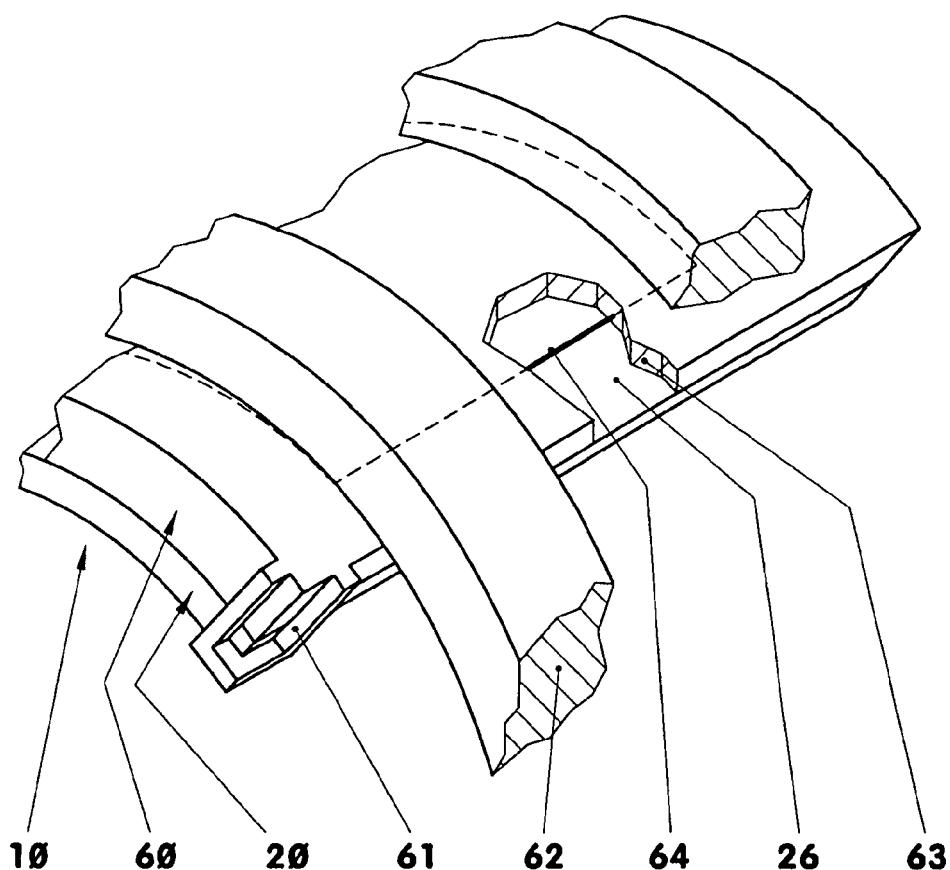
Figure 4:
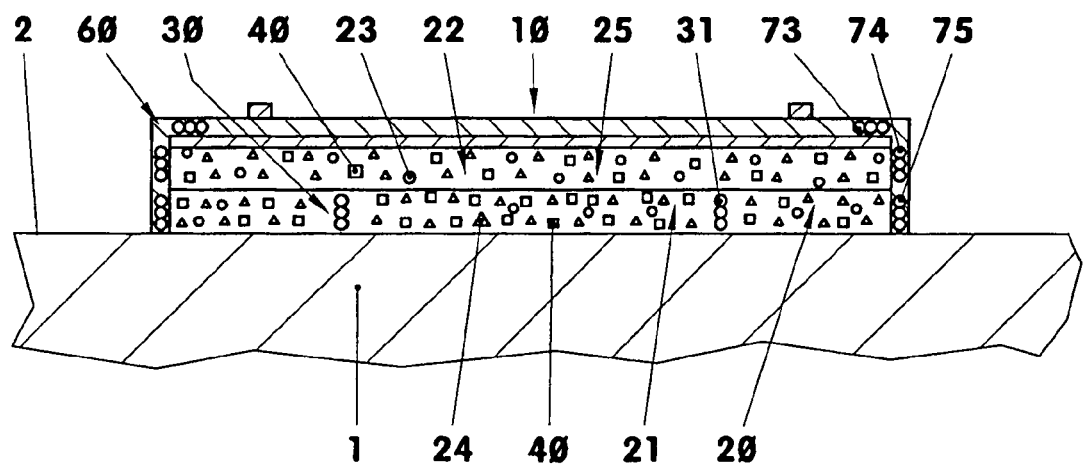
Figure 5:
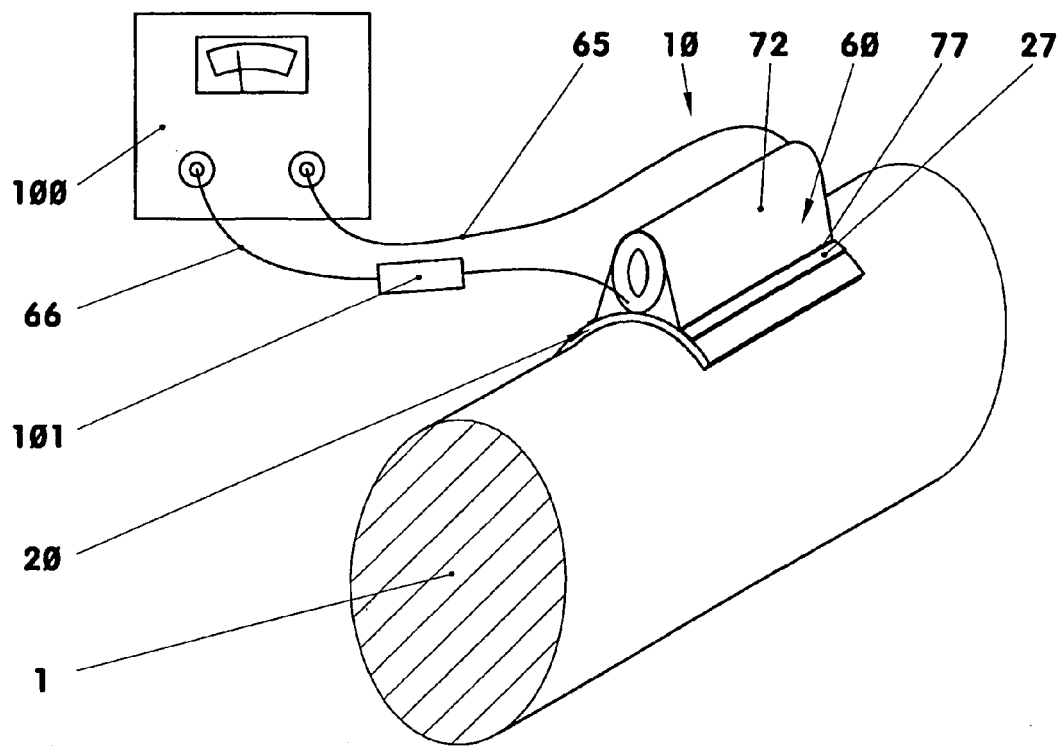
Figure 6:
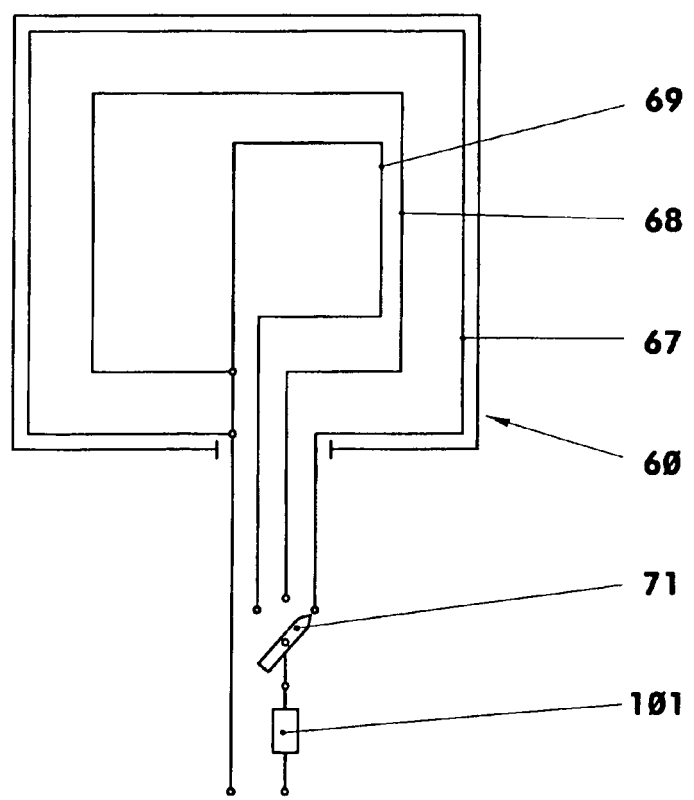
Figure 7:
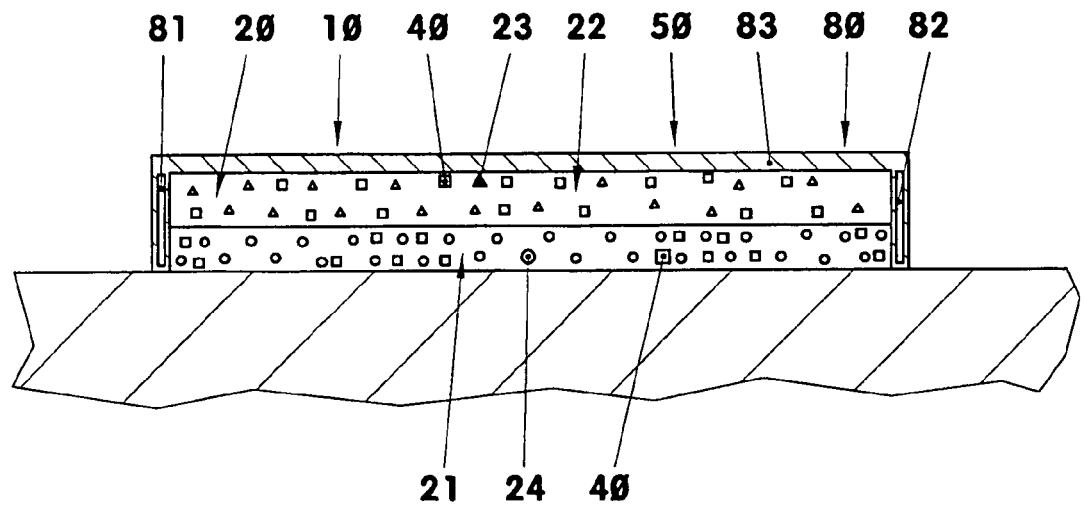
Figure 8:
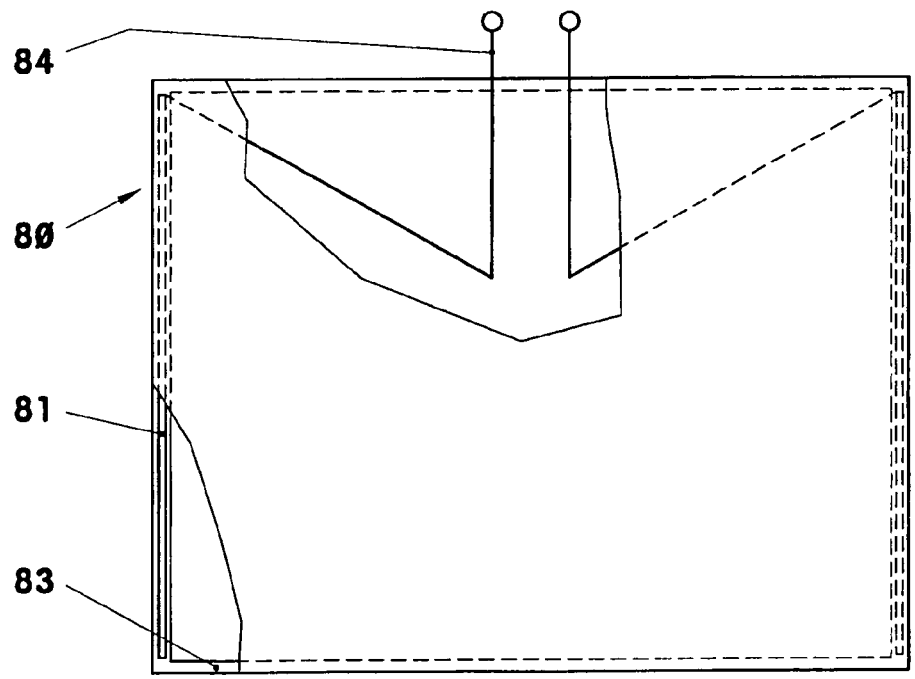

FIG. 1 shows a therapy device during operation.
FIG. 2 shows a partial longitudinal section through FIG. 1.
FIG. 3 shows a detail of the therapy device from FIG. 1.
FIG. 4 shows a partial longitudinal section through a therapy device with a therapeutic system with an integrated induction coil and a removable induction system.
FIG. 5 shows a therapy device with a cylindrical coil.
FIG. 6 shows an induction system.
FIG. 7 shows a therapy device with a capacitive system.
FIG. 8 shows a plan view of a capacitive system.

FIGS. 1 and 2 show, in dimetric projection, a longitudinal section of a therapy device (10) in use, e.g. on an arm (1) of a patient. In this exemplary embodiment, the therapy device (10) comprises a therapeutic system (20) and a system (50) that can be actuated electrically in a time-varying fashion. The electrically actuatable system (50) is e.g. an induction system (60). The latter is detachably connected to the therapeutic system (20) in a force-fit and/or interlocking fashion.

The therapeutic system (20) has a laminate design made of e.g. a plurality of mutually congruent laminate layers (21, 22). In the exemplary embodiment, it comprises, for example, an adhesive laminate layer (21) facing the skin (2) of the patient and an active-ingredient-containing upper laminate layer (22), which is congruent to said former laminate layer (21). On the side facing away from the skin (2) of the patient, the therapeutic system (20) is covered e.g. by means of a cover film (26) that protects the therapeutic system (20).

The therapeutic system (20) can optionally comprise only a single laminate layer. Said layer then is both the adhesive, pressure-sensitive self-adhesive layer and the active-ingredient-containing layer.

The adhesive, pressure-sensitive self-adhesive laminate layer (21) for example is a lipophilic, semi-solid adhesive. It is e.g. pressure sensitive. This means that the adhesive effect of the laminate layer (21) on the skin (2) is increased under the influence of an external pressure.

In the active-ingredient-containing laminate layer (22) of this transdermal therapeutic system (20), the active ingredients (23) are for example incorporated into a compound mass (25) with a gel-like consistency.

The pharmaceutical active-ingredient preparation (23) can also be embedded into the adhesive laminate layer (21). A transdermal therapeutic system (20) with a plurality of layers (22) arranged e.g. one over the other is also feasible. Optionally, the therapeutic system (20) can be embodied without an active-ingredient-containing layer (22). By way of example, it then serves as an active-ingredient-free patch for reducing pain by heat therapy.

In this exemplary embodiment, the transdermal therapeutic system (20) has a square surface area with an edge length of 70 millimeters. However, the surface area can also be rectangular, round, etc. Here, the system (20) has a thickness of e.g. between 50 and 300 micrometers.

By way of example, superparamagnetic nanoparticles (40) are incorporated into the active-ingredient-containing layer (22). Said nanoparticles are e.g. ferrimagnetic particles made of magnetite ($Fe_3O_4$) or maghemite ($\gamma$-$Fe_2O_3$). However, the particles can also consist of a material from the oxide ceramic group of ferrites. The grain size of the individual crystals lies between five nanometers and thirty nanometers. Optionally, the superparamagnetic nanoparticles (40) can also be designed like a rod or a wire. In the case of a single-layer transdermal therapeutic system (20), the superparamagnetic nanoparticles (40) are also incorporated into this layer.

At first, these crystals are magnetically neutral. However, they are magnetically aligned in an external magnetic field. Due to their small size, the crystals usually have only one so-called Weiss domain of the same magnetic orientation. The alignment of this domain follows the magnetic field lines of the external magnetic field. There is no hysteresis in this case and, accordingly, no remanence either. When the external magnetic field is switched off, the crystal once again is magnetically neutral.

The concentration of the superparamagnetic nanoparticles (40) in the respective laminate layer (21, 22) can lie between 0.5 percent by weight and 25 percent by weight. By way of example, it lies between one and 15 percent by weight. In the exemplary embodiment, the concentration of the superparamagnetic nanoparticles (40) lies between two and ten percent by weight of the upper laminate layer (22). Here, the concentration of the superparamagnetic nanoparticles (40) can be uniform throughout the entire therapeutic system (20), or the individual laminate layers (21, 22) have unequal concentrations.

By way of example, the cover film (26) is mechanically tearproof and impermeable for the active ingredient, the aroma and moisture. Hence the transdermal therapeutic system (20) is protected against damage and unwanted active-ingredient losses, even during prolonged use.

The induction system (60) rests on the cover film (26) of the therapeutic system (20) and, in the illustration of FIG. 1, is secured on the arm (1) of the patient by means of two securing bands (62). The latter are each closed by means of a detachable fastener (76). The position of the induction system (60) relative to the therapeutic system (20) is secured by means of, for example, two securing clamps (61) arranged diagonally opposing one another, cf. FIG. 3.

In the illustrated exemplary embodiment, the induction system (60) comprises e.g. a film-like coil former (63) and an induction coil (64) embedded in the coil former (63). By way of example, the induction coil (64) is embodied as a conductor loop with one winding. The end face of the induction coil (64) e.g. is at a constant distance from the skin (2) of the patient. The induction coil (64) can also have more than one winding and/or one coil core.

Two electrical lines (65, 66) connect the induction system (60) to an alternating-current source (100) via a series resistor (101). However, a direct-current source with a downstream inverter can also be used as a current source. Said inverter can, for example, be integrated into the induction system (60).

In order to use the therapeutic system (20), the latter is stuck onto the arm (1) of a patient, for example after removing a protective film from the adhesive laminate layer (21). Subsequently, the active ingredient (23) from the active-ingredient-containing layer (22), for example, passes through the adhesive layer (21) and into the skin (2) of the patient, and also through the skin of the latter, depending on the type of active-ingredient molecules. At first, the superparamagnetic nanoparticles (40) do not influence this procedure.

If the active-ingredient delivery into the skin (2), or the active-ingredient transport through the latter, is intended to be increased, the induction system (60) is firstly fixed onto the therapeutic system (20), e.g. by means of the securing clamps (61), and it is detachably attached to the arm (1) of the patient by means of the securing bands (62). The power source (100), which, for example, supplies a constant value of the effective alternating current at a constant frequency, is now switched on. The effective value of the voltage is the square of the mean value of the time-varying voltage value. The resulting current, the voltage and the frequency lie below a threshold that could be dangerous to the human body or that could cause side effects if the electrically conducting parts are inadvertently touched.

When the induction system (60) is in operation, the current flowing through the coil (64) causes the build-up of a magnetic field around the conductor through which the current flows. All dipoles in the magnetic field attempt to align in the direction of the field lines. The magnetic field strength increases with the current and with an increasing ratio of winding number to coil length. In an alternating-current circuit, the impedance and the time derivatives of the magnetic flux and the magnetic flux density in an induction coil (64) increase with an increasing frequency.

When an alternating current is applied, the magnetic field changes with time. The field changes both in terms of magnitude and direction. It penetrates the superparamagnetic nanoparticles (40). This changes the polarization direction of the superparamagnetic nanoparticles (40), which are fixedly incorporated in the compound mass (25). The frequency of the change in polarization corresponds to the frequency of the alternating current emitted by the current source (100). Some of the energy absorbed in the process by the superparamagnetic nanoparticles (40) is emitted as heat to the close vicinity thereof.

The thermal energy, released in the active-ingredient-containing laminate layer (22) in the exemplary embodiment, brings about the heating of said layer. By way of example, this brings about an increased diffusion of the dissolved active ingredient (23) within the system and toward the skin. An active ingredient, initially present in an undissolved form, can, for example, also be dissolved. This can increase the diffusion rate of the therapeutic system (20) and can, for example, make better use of the active ingredient (23).

The heat development, and hence the increase in the diffusion rate, are dependent on the supplied energy and the magnetic flux density of the induction system (60). In order to modify the supplied energy, there can be a change in e.g. the frequency of the alternating current, the effective voltage, the effective current or the switched-on period of the current source (100). By way of example, the amount of energy per unit time emitted by the superparamagnetic nanoparticles (40) increases as the current in the induction system (60) increases and as the frequency of the alternating current increases. In order to increase the effective current intensity in the circuit connected to the current source (100), there can, for example at a constant effective voltage, be a reduction in the series resistor and/or the reactance.

By way of example, the magnetic flux density of the induction system can be increased by means of a coil core. Since the magnetic-flux-density vector depends on the direction and the magnitude of the excitation current at all times, the magnetic flux density changes with the applied alternating current.

Hence, the active-ingredient delivery into the skin (2) of the patient, and/or the active-ingredient transport through the skin (2) of the latter, can be controlled by means of the current source (100) and by means of the induction system (60).

The heat generation is stopped as soon as the current source is switched off. The diffusion rate of the active ingredient (23) decreases until it has once again reached its initial value. Once the securing bands (62) have been detached, the induction system (60) can be removed from the therapeutic system (20) and from the arm (1) of the patient.

In the case of a therapeutic system (20) with the skin-contacting laminate layer (21) thereof containing superparamagnetic nanoparticles (40), heating said layer allows the skin (2) in the vicinity of the contact zone to be heated in a targeted manner. This accelerates the active-ingredient transport into the skin (2) and through the latter. Targeted heating of the skin contact layer can also be used therapeutically, for example if used as an active-ingredient-free thermal patch. By way of example, this can treat rheumatic ailments, such as sciatica, lumbago, neck stiffness, shoulder/arm pain, etc.

Once the induction system (60) has been switched off, and optionally removed, the therapeutic system (20) can remain on the arm (1) and need not be removed. After the induction system (60) has been put on again, the heat supply and/or active-ingredient supply can be increased again. Thus, if required, heat therapy or, in the case of active-ingredient-containing systems, a time-limited dose increase can for example be applied several times a day. Here the temperature can be individually controlled.

By way of example, if a plurality of therapeutic systems (20) are arranged on the body, they can successively be connected to the same induction system (60). It is also feasible for differently designed induction systems (60) to be connected to one therapeutic system (20). This affords the possibility of e.g. making different zones of the therapeutic system (20) respond, depending on the requirements. It is also feasible for the therapy device (10) to be operated at different energy levels.

FIG. 4 shows a therapy device (10) with two induction systems (30, 60). A first induction system (60), which can be removed from the therapeutic system (20), has been placed onto the therapeutic system (20) in a cap-like fashion. In this exemplary embodiment, this induction system (60) comprises three coils (73-75). A first coil (73), with three spirally arranged windings, is arranged e.g. above the therapeutic system (20). In this exemplary embodiment, the other two coils (74, 75) are arranged, for example one over the other, around the end faces of the therapeutic system (20). By way of example, in this case an upper induction coil (74) is arranged around the upper laminate layer (22) and a lower induction coil (75) is arranged around the adhesive layer (21). By way of example, these coils (73-75) can be used to target individual laminate layers (21, 22), for example to increase the active-ingredient diffusion in an individual layer (21, 22).

The second induction system (30) is integrated into the therapeutic system (20). In this exemplary embodiment, this induction system (30) comprises a centrally arranged coil (31). By way of example, in the illustration of FIG. 4, the coil cross-sectional area is arranged parallel to the skin (2). The coil (31) is electrically connected to the first induction system (60), for example by means of a spring-loaded contact connection (not illustrated here). By way of example, it can be switched on or off by means of a switch. When connected into the circuit, it can be operated on its own or in parallel with one or more other coils (73-75).

If the coil (31) of the second induction system (30) is switched off or electrically separated when the first induction system (60) is switched on, the magnetic field built up by the first induction system (60) influences the second induction system (30). The time-varying magnetic field of the first induction system (60) penetrates the coil (31) integrated into the therapeutic system (20). Alternating currents are induced in this coil (31). As a result, the coil emits heat. The surroundings of the coil (31) are heated. Said coil, together with the superparamagnetic nanoparticles (40), now contributes to the change in the active-ingredient diffusion and/or to the temperature increase for therapeutic purposes.

In the exemplary embodiment illustrated in FIG. 4, two active ingredients (23, 24) are incorporated with different concentrations. After the e.g. separate production in an active-ingredient-containing laminate layer (22) and in an adhesive laminate layer (21), the concentration has been set in accordance with the solubility in the individual layers (21, 22). Superparamagnetic nanoparticles (40) are embedded with different concentrations in both laminate layers (21, 22). Optionally, the superparamagnetic nanoparticles (40) can also be incorporated in only one of the two layers (21, 22).

The two induction systems (60, 30) can be used for targeted control of the active-ingredient delivery by the therapeutic system (20), for example in the case where a partly undissolved active ingredient (23, 24) is present. This can change the concentration ratio of the active ingredients (23, 24) with respect to one another, or the diffusion rate of one of the active ingredients (23, 24) can be increased.

By way of example, if one of the active ingredients (23; 24) or if both of the active ingredients (23, 24) is or are present in a largely undissolved state, the undissolved proportion or the undissolved proportions is or are not available for equalizing the concentration or for passive diffusion. The superparamagnetic nanoparticles (40) are arranged either in one of the two laminate layers (21; 22) or in both laminate layers (21, 22), for example with different concentrations.

After the transdermal therapeutic system (20) has been stuck onto the skin, it is only e.g. the dissolved first active ingredient that is delivered to the skin.

After the electrically actuatable system (50) has been switched on, the temperature increase, for example to temperatures far above the body temperature, leads to a dissolving of the second active ingredient, which is initially present in an undissolved form. This active ingredient now is likewise available for diffusion.

The concentration-equalization between the two laminate layers (21, 22) can also be influenced by means of a control membrane, which, for example, is embodied as an intermediate layer and which e.g. is semi-permeable. Superparamagnetic nanoparticles (40) can be incorporated into this control membrane, in addition to in the laminate layers (21, 22) or as an alternative thereto.

FIG. 5 illustrates a therapy device (10), the induction system (60) of which comprises a cylindrical coil (72). By way of example, this longitudinal coil (72) comprises two hundred windings. The magnetic realignment of the individual superparamagnetic nanoparticles (40) is virtually instantaneous on account of the rapid change in the magnetic flux density. As a result, the superparamagnetic nanoparticles (40) can release large amounts of energy. By way of example, the induction system (60) comprises lateral guide rails (77), by means of which it sits in plug-in guides (27) of the therapeutic system (20) and butts against a stop (not illustrated). The cylindrical coil (72) can also have a coil core.

FIG. 6 illustrates an induction system (60) with e.g. three induction coils (67-69) and with a switch (71). By way of example, the coils (67-69) are arranged boxed within one another and have e.g. different cross-sectional areas. By way of example, the cross-sectional area of the outer coil (67) corresponds to the size of the surface of the therapeutic system (20). When this induction coil (67) is in operation, for example all superparamagnetic nanoparticles (40) arranged in the therapeutic system (20) are made to respond.

The central coil (68) is situated within this outer coil (67). By way of example, the cross-sectional area of said central coil is half of the cross-sectional area of the outer coil. This central coil (68) can be used to concentrate the energy delivery to the central region of the therapeutic system (20).

In the plan view of FIG. 6, the inner coil (69) is situated in e.g. the right-hand region of the central coil (68). The cross-sectional area of said inner coil is for example 15% of the cross-sectional area of the outer coil (67). If this inner coil (69) is actuated electrically, it is predominantly the superparamagnetic nanoparticles (40) in the right-hand region of the therapeutic system (20) that are excited. The heat development then occurs in this region, which heat development accelerates the active-ingredient diffusion or enables heat therapy.

The individually illustrated coils (67-69) can each have more than one winding. The use of one or more coil cores is also feasible.

By way of example, if the concentration of the superparamagnetic nanoparticles (40) is higher in the right-hand region of the therapeutic system (20) than in the other regions of the therapeutic system (20), the illustrated inner coil (69) for example temporarily enables a concentrated heat supply. The therapeutic system (20) can comprise a separate laminate layer in said right-hand region for this purpose.

It is also feasible for two coils (67, 68; 67, 69; 68, 69), or all coils (67-69), to be actuated simultaneously in the induction system (60) illustrated in FIG. 6. The magnetic fields of the coils (67-69) interact. In some regions, the magnetic field of the entire induction system (60) is amplified; in other regions it is attenuated. It is also feasible for each coil (67; 68; 69) to be actuated individually at the same time, e.g. with differing frequencies. Due to the resulting beats and resonances in the excitation frequencies, the temperature of the individual regions of the therapeutic system (20) oscillates during the period of the treatment. Optionally, this can generate e.g. a circulating or discontinuous temperature maximum.

FIG. 7 illustrates a therapy device (10) with a therapeutic system (20) and an electrically actuatable system (50) designed as a capacitive system (80).

By way of example, the therapeutic system (20) is embodied as described in conjunction with FIGS. 1 to 6. The active ingredient (23) and the superparamagnetic nanoparticles (40) are incorporated in both the upper laminate layer (22) and the adhesive laminate layer (21) with a different concentration that is not constant over the sectional plane of FIG. 7.

The capacitive system (80) comprises e.g. two mutually opposing capacitor plates (81, 82), between which the therapeutic system (20) is arranged. By way of example, the capacitive system (80) is connected to the therapeutic system (20) by means of a detachable force-fit and/or interlocking connection, e.g. by means of suction cups.

FIG. 8 shows a plan view onto such a capacitive system (80). The capacitor plates (81, 82) are embedded in a capacitor carrier (83). They can be connected to an alternating-current source (100) by means of the connection lines (84).

The electrical impedance of a capacitive system (80) incorporated into an alternating-current circuit falls with increasing alternating-current-source (100) frequency. The time derivative of the charge of the capacitor plates (81, 82) and the time derivative of the electric displacement field increase with increasing frequency.

A time-varying electric field is generated between the capacitor plates (81, 82), after the capacitive system (80) has been connected to an alternating-current source (100). The therapeutic system (20) with the incorporated superparamagnetic nanoparticles (40) forms the dielectric. The alternating electric field brings about an alternating polarity in the superparamagnetic nanoparticles (40). The superparamagnetic nanoparticles (40) emit some of the energy they have absorbed from the electric field as heat. By way of example, the increase in temperature in the system leads to increased diffusion coefficients of the active ingredients in the preparations and hence it leads to an improved active-ingredient delivery.

In order to increase further the heat emitted by the superparamagnetic nanoparticles (40), it is possible, for example, to increase the voltage applied to the capacitive system (80). It is also possible to arrange an additional dielectric or to modify the frequency of the alternating-current source (100) in order to change the heat emission e.g. in the capacitive system (80) and/or in the therapeutic system (20).

The electric field is switched off when the alternating-current source (100) is switched off. The superparamagnetic nanoparticles (40) assume their most energy-favorable state. They no longer emit heat. The diffusion rate of the active ingredients (23, 24) in the therapeutic system (20) falls to its initial value.

It is also feasible for the electrically actuatable device (50) of the therapy device (10) to comprise both a capacitive system (80) and an inductive system (60). By way of example, these could be switched on alternately such that e.g. different zones of the therapeutic system are made to respond.

Combinations of the various embodiments are also feasible.

LIST OF REFERENCE SIGNS

1 Arm
2 Skin
10 Therapy device
20 Therapeutic system, transdermal therapeutic system
21 Adhesive laminate layer, laminate layer
22 Upper laminate layer, laminate layer
23 Active ingredient, first active ingredient. Pharmaceutical active-ingredient preparation
24 Second active ingredient
25 Compound mass
26 Cover film
27 Plug-in guide
30 Second induction system
31 Coil, internal
40 Superparamagnetic nanoparticle
50 Electrically actuatable system
60 Induction system
61 Securing clamps, closure part
62 Securing bands, closure part
63 Coil former
64 Induction coil, coil
65, 66 Lines
67 Outer induction coil
68 Central induction coil
69 Inner induction coil
71 Switch
72 Cylindrical coil, longitudinal coil
73 Induction coil
74 Induction coil, top
75 Induction coil, bottom
76 Fastener
77 Guide rail
80 Capacitive system
81 Capacitor plate
82 Capacitor plate
83 Capacitor carrier
84 Connection lines
100 Alternating-current source
101 Series resistor

The invention claimed is:

1. A therapy device comprising:
   a therapeutic system, which has a laminate design, comprising:
   at least one adhesive laminate layer;
   at least one superparamagnetic-nanoparticle-containing layer which comprises superparamagnetic nanoparticles; and
   a protective layer;
   where the at least one superparamagnetic-nanoparticle-containing layer is:
   a second laminate layer; or
   an intermediate layer arranged between the at least one adhesive laminate layer and the second laminate layer; and
   at least one electrically actuatable system integrated in or detachably connected to the therapeutic system;
   wherein the at least one electrically actuatable system has a frequency-dependent electrical impedance;
   wherein, during the operation of the therapy device, the at least one electrically actuatable system generates an electric or magnetic field, which varies over time in orientation and magnitude and which penetrates the superparamagnetic nanoparticles so that the superparamagnetic nanoparticles penetrated by the electric or magnetic field heat up the superparamagnetic-nanoparticle-containing layer; and
   wherein the superparamagnetic nanoparticles are magnetically neutral when the electric or magnetic field is switched off.

2. The therapy device as claimed in claim 1;
   wherein the superparamagnetic nanoparticles have a maximum extent of between five and thirty nanometers.

3. The therapy device as claimed in claim 1;
   wherein the mass of all the superparamagnetic nanoparticles incorporated in the at least one superparamagnetic-nanoparticle-containing layer is between 0.5 percent and 25 percent of the mass of the superparamagnetic-nanoparticle-containing layer.

4. The therapy device as claimed in claim 1;
   wherein the therapeutic system includes the second laminate layer, which is an active-ingredient-containing layer.

5. The therapy device as claimed in claim 4;
   wherein superparamagnetic nanoparticles are embedded in the active-ingredient-containing layer.

6. The therapy device as claimed in claim 1;
   wherein the at least one electrically actuatable system comprises an integrated induction system integrated in the therapeutic system.

7. The therapy device as claimed in claim 1;
   wherein the at least one electrically actuatable system comprises a detachable induction system that is detachably connected to the therapeutic system.

8. The therapy device as claimed in claim 1;
   wherein the at least one electrically actuatable system comprises a capacitive system that is detachably connected to the therapeutic system.

9. The therapy device as claimed in claim 6;
   wherein the integrated induction system is integrated into the at least one superparamagnetic-nanoparticle-containing layer.

10. The therapy device as claimed in claim 6;
    wherein the integrated induction system is integrated into the at least one adhesive laminate layer.

11. The therapy device as claimed in claim 7;
    wherein the at least one electrically actuatable system further comprises an integrated induction system integrated into the therapeutic system.

12. The therapy device as claimed in claim 11;
    wherein the integrated induction system is integrated into the at least one superparamagnetic-nanoparticle-containing layer.

13. The therapy device as claimed in claim 11;
    wherein the integrated induction system is integrated into the at least one adhesive laminate layer.

14. The therapy device as claimed in claim 8;
    wherein the at least one electrically actuatable system further comprises an integrated induction system integrated into the therapeutic system.

15. The therapy device as claimed in claim 14;
    wherein the integrated induction system is integrated into the at least one superparamagnetic-nanoparticle-containing layer.

16. The therapy device as claimed in claim 14;
    wherein the integrated induction system is integrated into the at least one adhesive laminate layer.

17. A therapy device comprising:
    therapeutic system, which has a laminate design, comprising:
    at least one superparamagnetic-nanoparticle-containing layer which is an adhesive laminate layer, and which comprises superparamagnetic nanoparticles;
    a protective layer;
    optionally an additional adhesive laminate layer; and
    optionally a second laminate layer;
    where, optionally, the at least one superparamagnetic-nanoparticle-containing layer is an intermediate layer arranged between the additional adhesive laminate layer and the second laminate layer; and
    at least one electrically actuatable system integrated in or detachably connected to the therapeutic system;
    wherein the at least one electrically actuatable system has a frequency-dependent electrical impedance;
    wherein, during the operation of the therapy device, the at least one electrically actuatable system generates an electric or magnetic field, which varies over time in orientation and magnitude and which penetrates the superparamagnetic nanoparticles so that the superparamagnetic nanoparticles penetrated by the electric or magnetic field heat up the superparamagnetic-nanoparticle-containing layer; and
    wherein the superparamagnetic nanoparticles are magnetically neutral when the electric or magnetic field is switched off.

18. The therapy device as claimed in claim 17;
    wherein the superparamagnetic nanoparticles have a maximum extent of between five and thirty nanometers.

19. The therapy device as claimed in claim 17;
    wherein the mass of all the superparamagnetic nanoparticles incorporated in the at least one superparamagnetic-nanoparticle-containing layer is between 0.5 percent and 25 percent of the mass of the superparamagnetic-nanoparticle-containing layer.

20. The therapy device as claimed in claim 17;
    wherein the therapeutic system includes the second laminate layer, which is an active-ingredient-containing layer.

21. The therapy device as claimed in claim 17;
    wherein the at least one superparamagnetic-nanoparticle-containing layer contains an active ingredient.

22. The therapy device as claimed in claim 17;
wherein the at least one electrically actuatable system comprises an integrated induction system integrated in the therapeutic system.

23. The therapy device as claimed in claim 17;
wherein the at least one electrically actuatable system comprises a detachable induction system that is detachably connected to the therapeutic system.

24. The therapy device as claimed in claim 17;
wherein the at least one electrically actuatable system comprises a capacitive system that is detachably connected to the therapeutic system.

25. The therapy device as claimed in claim 22;
wherein the integrated induction system is integrated into the at least one superparamagnetic-nanoparticle-containing layer.

26. The therapy device as claimed in claim 22;
wherein the therapeutic system includes the additional adhesive laminate layer, and the integrated induction system is integrated into the additional adhesive laminate layer.

27. The therapy device as claimed in claim 23;
wherein the at least one electrically actuatable system further comprises an integrated induction system integrated into the therapeutic system.

28. The therapy device as claimed in claim 27;
wherein the integrated induction system is integrated into the at least one superparamagnetic-nanoparticle-containing layer.

29. The therapy device as claimed in claim 27;
wherein the therapeutic system includes the additional adhesive laminate layer, and the integrated induction system is integrated into the additional adhesive laminate layer.

30. The therapy device as claimed in claim 24;
wherein the at least one electrically actuatable system further comprises an integrated induction system integrated into the therapeutic system.

31. The therapy device as claimed in claim 30;
wherein the integrated induction system is integrated into the at least one superparamagnetic-nanoparticle-containing layer.

32. The therapy device as claimed in claim 30;
wherein the therapeutic system includes the additional adhesive laminate layer, and the integrated induction system is integrated into the additional adhesive laminate layer.

\* \* \* \* \*